US008773756B2

(12) United States Patent
Tesar et al.

(10) Patent No.: US 8,773,756 B2
(45) Date of Patent: Jul. 8, 2014

(54) COMPENSATING OPTICAL COUPLER FOR VISIBLE AND NIR IMAGING

(75) Inventors: John C. Tesar, Tucson, AZ (US); Paul Cottle, Vancouver (CA); John J. P. Fengler, North Vancouver (CA)

(73) Assignee: Novadaq Technologies Inc., Mississauga (CA)

( * ) Notice: Subject to any disclaimer, the term of this patent is extended or adjusted under 35 U.S.C. 154(b) by 323 days.

(21) Appl. No.: 13/122,770

(22) PCT Filed: Oct. 6, 2009

(86) PCT No.: PCT/US2009/059702
§ 371 (c)(1),
(2), (4) Date: Jun. 30, 2011

(87) PCT Pub. No.: WO2010/042522
PCT Pub. Date: Apr. 15, 2010

(65) Prior Publication Data
US 2011/0249323 A1   Oct. 13, 2011

Related U.S. Application Data

(60) Provisional application No. 61/103,012, filed on Oct. 6, 2008.

(51) Int. Cl.
*G02B 23/04* (2006.01)
*G02B 13/14* (2006.01)
(52) U.S. Cl.
CPC .................... *G02B 13/146* (2013.01)
USPC .......................................... 359/353
(58) Field of Classification Search
None
See application file for complete search history.

(56) References Cited

U.S. PATENT DOCUMENTS

| 4,597,630 | A  | * | 7/1986  | Brandstetter et al. ............. 359/9 |
| 5,973,315 | A  | * | 10/1999 | Saldana et al. ........... 250/214 VT |
| 6,181,414 | B1 | * | 1/2001  | Raz et al. ......................... 356/51 |
| 7,333,270 | B1 | * | 2/2008  | Pochapsky et al. ........... 359/634 |
| 2008/0237771 | A1 | * | 10/2008 | Pilla et al. ..................... 257/458 |

* cited by examiner

*Primary Examiner* — Derek S Chapel
(74) *Attorney, Agent, or Firm* — Oliff PLC

(57) ABSTRACT

An optical system, in particular for endoscopic applications, is disclosed which uses wavelength-compensating optical components, in particular prisms, made of materials with different inter-element coatings and refractive indices to image significantly different wavelength-ranges (VIS and NIR) onto the same image plane of an image acquisition device, such as a CCD sensor.

19 Claims, 10 Drawing Sheets

Diagrams:

2-channel prism 3-channel prism 4-channel prism 4-channel prism rotated 90 degrees

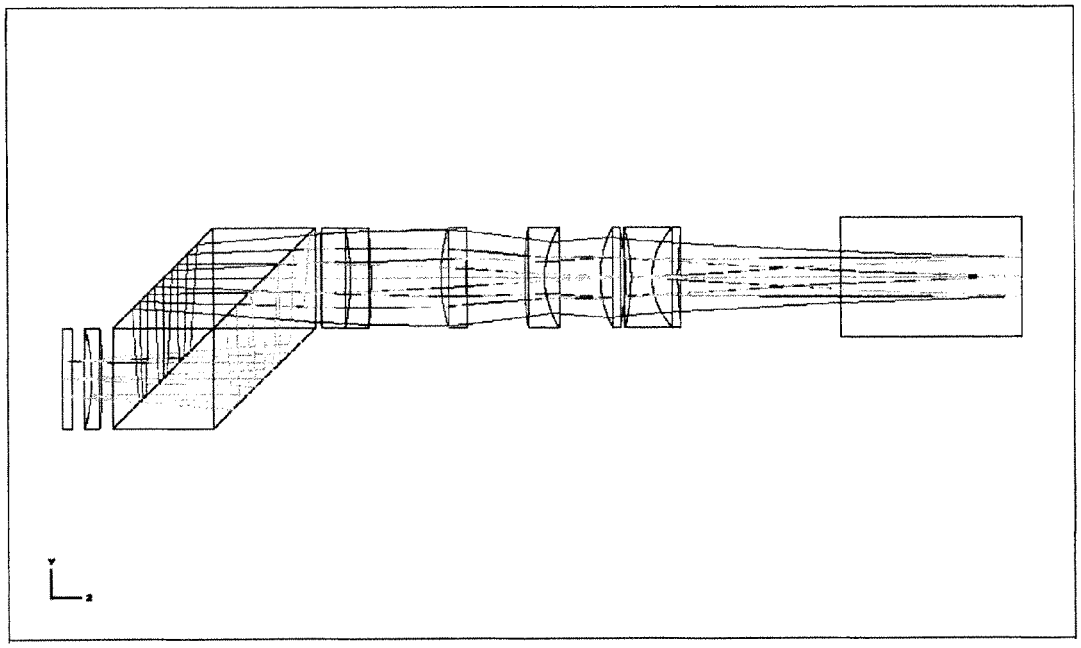
FIG. 6a Combined VIS NIR
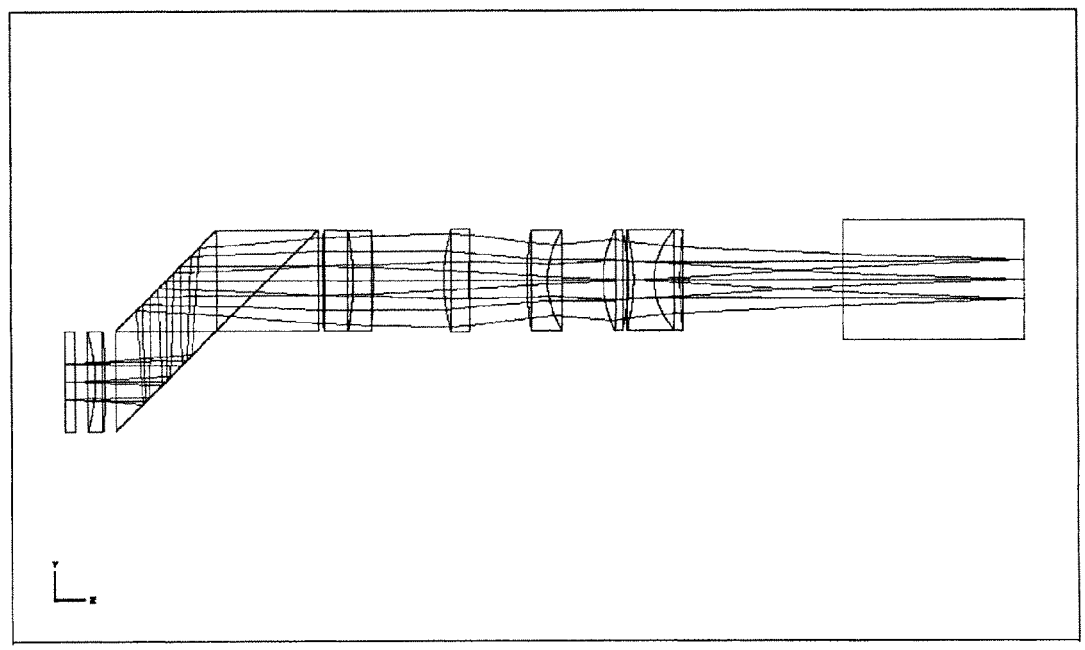
FIG. 6b VIS only

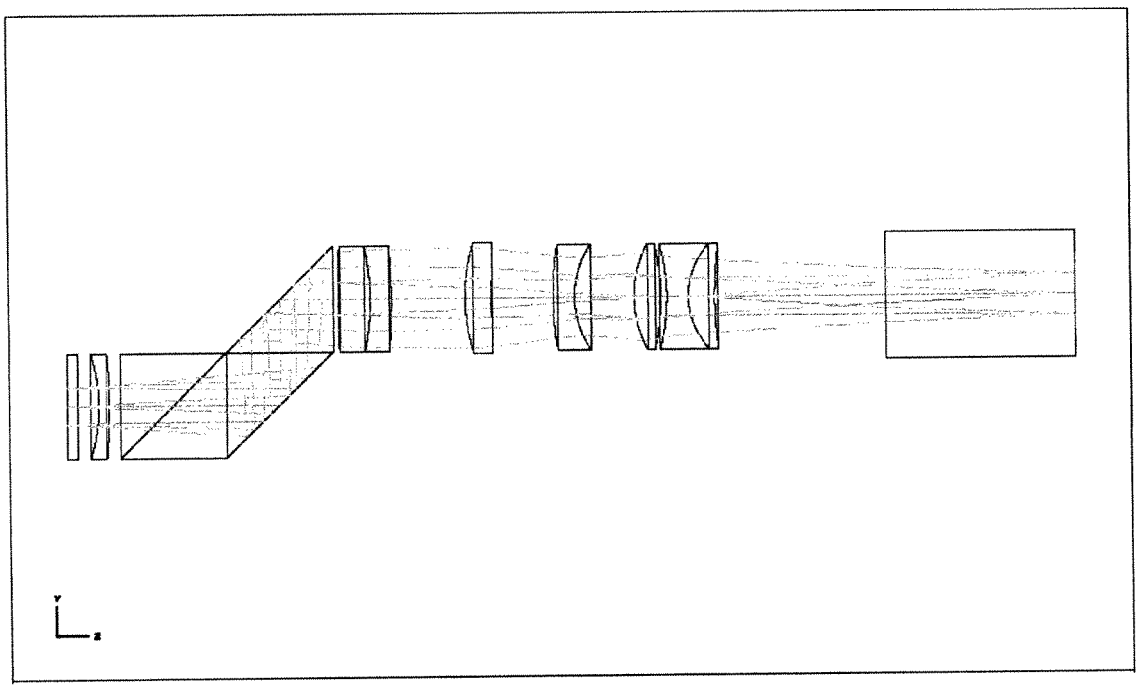
FIG. 6c  NIR only

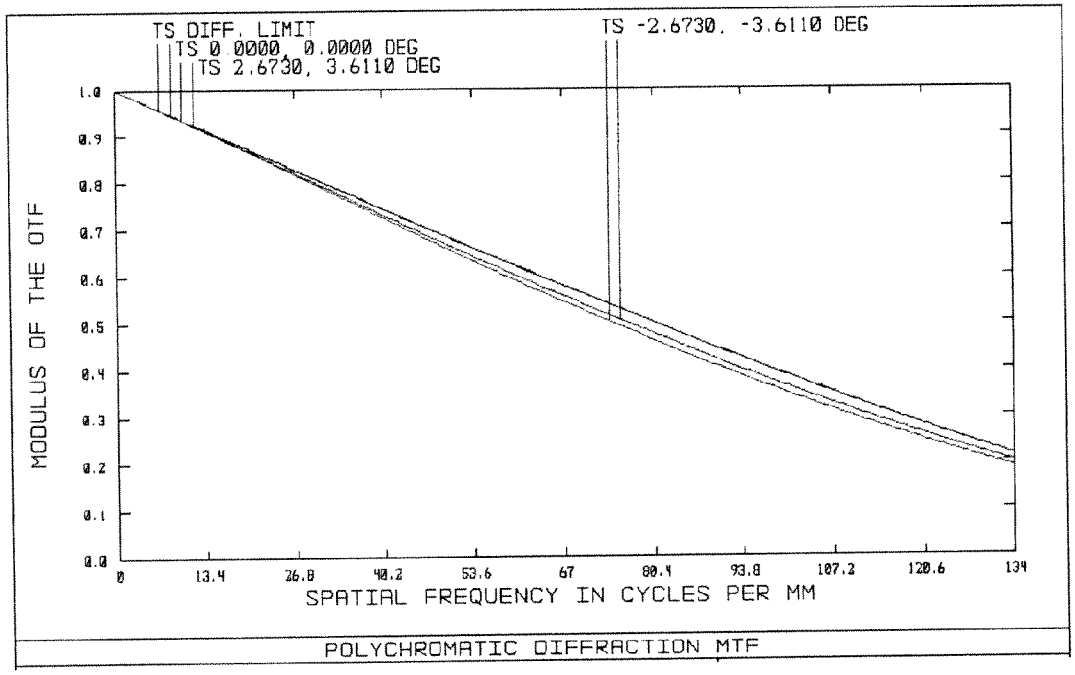
FIG. 6d  VIS (486 nm- 656 nm)
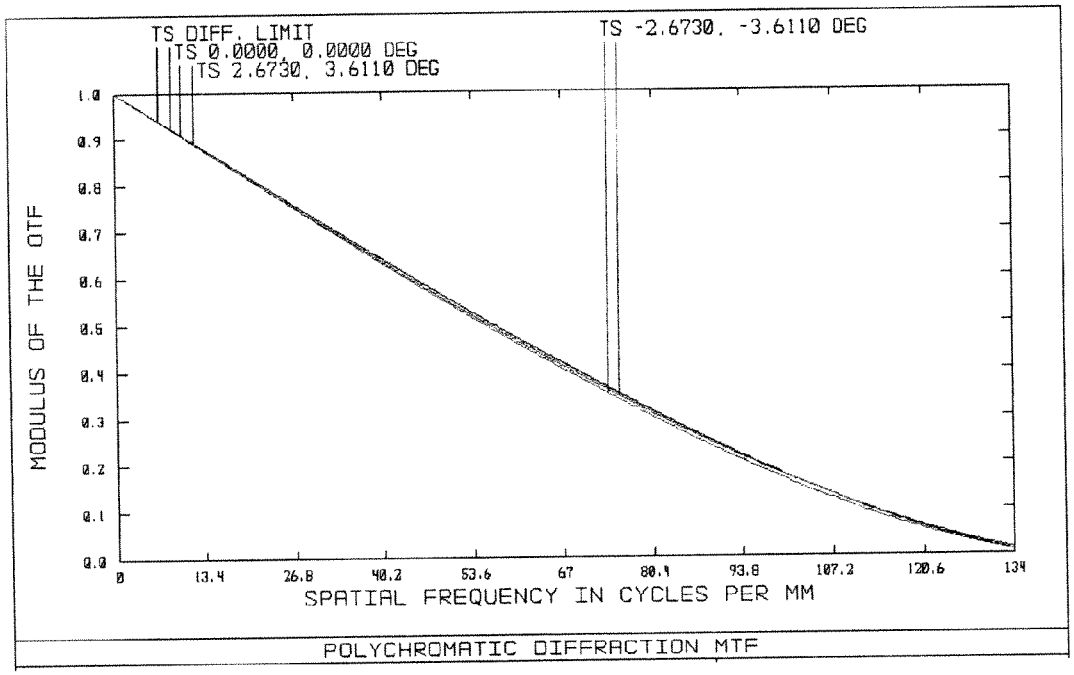
FIG. 6e  NIR (830nm – 850nm)

SURFACE DATA SUMMARY FOR VIS:

| Surf | Type | Radius | Thickness | Glass | Diameter | Conic | Comment |
|---|---|---|---|---|---|---|---|
| STO | STANDARD | Infinity | 0 |  | 3.6 | 0 |  |
| 2 | STANDARD | Infinity | 0 |  | 3.6 | 0 |  |
| 3 | STANDARD | Infinity | 1 | SAPPHIRE | 10 | 0 | endoscope window |
| 4 | STANDARD | Infinity | 2 |  | 10 | 0 |  |
| 5 | STANDARD | -17.438 | 1 | N-LAF34 | 10 | 0 | afocal 1 |
| 6 | STANDARD | -52.38 | 1 |  | 10 | 0 |  |
| 7 | STANDARD | Infinity | 5 | SF11 | 10 | 0 | compensating prism |
| 8 | COORDBRK | - | 0 | - | - |  |  |
| 9 | STANDARD | Infinity | 0 | MIRROR | 10 | 0 |  |
| 10 | COORDBRK | - | -5 | - | - |  |  |
| 11 | STANDARD | Infinity | -5 | SF11 | 10 | 0 |  |
| 12 | COORDBRK | - | 0 | - | - |  |  |
| 13 | STANDARD | Infinity | 0 | MIRROR | 10 | 0 |  |
| 14 | COORDBRK | - | 5 | - | - |  |  |
| 15 | STANDARD | Infinity | 5 | BK7 | 10 | 0 |  |
| 16 | COORDBRK | - | 0 | - | - |  |  |
| 17 | STANDARD | Infinity | 0 | BK7 | 10 | 0 |  |
| 18 | COORDBRK | - | 5 | - | - |  |  |
| 19 | STANDARD | Infinity | 0.5 |  | 10 | 0 |  |
| 20 | STANDARD | 97 | 3 | N-LAK33A | 10 | 0 | afocal |
| 21 | STANDARD | -24.95 | 2 | KZFSN5 | 10 | 0 |  |
| 22 | STANDARD | -58.17 | 7 |  | 10 | 0 | adjustment space |
| 23 | STANDARD | 18.19 | 2.5 | N-PK51 | 10.24504 | 0 |  |
| 24 | STANDARD | 232.7 | 5.748 |  | 9.936443 | 0 |  |
| 25 | STANDARD | 31.03 | 2 | N-LAK8 | 10 | 0 |  |
| 26 | STANDARD | 9.484 | 5.44 |  | 10 | 0 |  |
| 27 | STANDARD | 10.91 | 2.5 | N-PSK53 | 10 | 0 |  |
| 28 | STANDARD | -23.09 | 0.549 |  | 10 | 0 |  |
| 29 | STANDARD | -19.33 | 2 | KZFSN5 | 10 | 0 |  |
| 30 | STANDARD | 7.2 | 2.5 | F5 | 10 | 0 |  |
| 31 | STANDARD | 34.567 | 16 |  | 10 | 0 | adjustment space |
| 32 | STANDARD | Infinity | 17.83 | N-BAK2 | 12 | 0 | 3 channel prism |
| 33 | STANDARD | Infinity | 0.04 |  | 12 | 0 |  |
| IMA | STANDARD | Infinity | 0 |  | 4.88 | 0 | CCD |

FIG. 7a

SURFACE DATA SUMMARY FOR NIR:

| Surf | Type | Radius | Thickness | Glass | Diameter | Conic | Comment |
|---|---|---|---|---|---|---|---|
| STO | STANDARD | Infinity | 0 | | 3.6 | 0 | |
| 2 | STANDARD | Infinity | 0 | | 3.6 | 0 | |
| 3 | STANDARD | Infinity | 1 | SAPPHIRE | 10 | 0 | endoscope window |
| 4 | STANDARD | Infinity | 2 | | 10 | 0 | |
| 5 | STANDARD | -17.438 | 1 | N-LAF34 | 10 | 0 | afocal 1 |
| 6 | STANDARD | -52.38 | 1 | | 10 | 0 | |
| 7 | STANDARD | Infinity | 5 | SF11 | 10 | 0 | compensating prism |
| 8 | COORDBRK | - | 0 | - | - | | |
| 9 | STANDARD | Infinity | 0 | SF11 | 10 | 0 | |
| 10 | COORDBRK | - | 5 | - | - | | |
| 11 | STANDARD | Infinity | 5 | BK7 | 10 | 0 | |
| 12 | COORDBRK | - | 0 | - | - | | |
| 13 | STANDARD | Infinity | 0 | MIRROR | 10 | 0 | |
| 14 | COORDBRK | - | -5 | - | - | | |
| 15 | STANDARD | Infinity | -5 | BK7 | 10 | 0 | |
| 16 | COORDBRK | - | 0 | - | - | | |
| 17 | STANDARD | Infinity | 0 | MIRROR | 10 | 0 | |
| 18 | COORDBRK | - | 5 | - | - | | |
| 19 | STANDARD | Infinity | 0.5 | | 10 | 0 | |
| 20 | STANDARD | 97 | 3 | N-LAK33A | 10 | 0 | afocal 2 |
| 21 | STANDARD | -24.95 | 2 | KZFSN5 | 10 | 0 | |
| 22 | STANDARD | -58.17 | 7 | | 10 | 0 | adjustment space |
| 23 | STANDARD | 18.19 | 2.5 | N-PK51 | 10.54976 | 0 | |
| 24 | STANDARD | 232.7 | 5.748 | | 10.23414 | 0 | |
| 25 | STANDARD | 31.03 | 2 | N-LAK8 | 10 | 0 | |
| 26 | STANDARD | 9.484 | 5.44 | | 10 | 0 | |
| 27 | STANDARD | 10.91 | 2.5 | N-PSK53 | 10 | 0 | |
| 28 | STANDARD | -23.09 | 0.549 | | 10 | 0 | |
| 29 | STANDARD | -19.33 | 2 | KZFSN5 | 10 | 0 | |
| 30 | STANDARD | 7.2 | 2.5 | F5 | 10 | 0 | |
| 31 | STANDARD | 34.567 | 16 | | 10 | 0 | adjustment space |
| 32 | STANDARD | Infinity | 17.83 | N-BAK2 | 12 | 0 | 3 channel prism |
| 33 | STANDARD | Infinity | 0.04 | | 12 | 0 | |
| IMA | STANDARD | Infinity | 0 | | 4.75 | 0 | CCD |

FIG. 7b

COMPENSATING OPTICAL COUPLER FOR VISIBLE AND NIR IMAGING

BACKGROUND

Near-infrared (NIR) imaging using endoscopes has been described in the literature for various clinical applications. Typically, such an imaging modality utilizes a contrast agent (e.g. indocyanine green) that absorbs and/or fluoresces in the 700-900 nm range of the NIR. In some endoscopic imaging systems capable of high resolution simultaneous color and NIR imaging, none of the image sensors (if multiple image sensors are used) or specific pixels of an image sensor (if only a single color image sensor is used) are exclusively dedicated to NIR imaging. One exemplary imaging system, described in the Annex of the present disclosure, utilizes a red, green, blue (RGB) sensor assembly to acquire both color and NIR fluorescence images by employing the red image sensor to, alternately and in rapid succession, acquire both the red light required for the color image and NIR light required for the NIR image. This imaging system is intended to be used in conjunction with image-projecting optical instruments such as endoscopes, microscopes, colposcopes, etc. that have also been optimized for both visible light and NIR imaging applications. Specifically the optical instruments (i.e. endoscopes, microscopes, colposcopes, etc.) and the optical assemblies (optical couplers) that couple these instruments to the sensor assembly of the imaging system are constructed using appropriate visible and NIR transmitting optical materials and anti-reflection coatings and are optically designed to transmit visible and NIR images for which chromatic and geometric aberrations are minimized. FIG. 1 depicts a typical configuration of an optical instrument, optical coupler and imaging system such as that being described above.

Although the preponderance of optical instruments currently in use are not optimized for both visible (VIS) and NIR light imaging, such instruments may still transmit sufficient NIR light that it may also be desirable to enable the previously described VIS-NIR imaging system for use with these conventional optical instruments. Conventional optical instruments are typically well-corrected for imaging throughout the visible spectrum, but without equivalent correction in the NIR, NIR images acquired with the aforementioned VIS-NIR imaging system through such optical instruments are likely to be of poor quality. Furthermore, although some of the NIR image aberrations introduced by conventional optical instruments may be corrected by applying compensating lens design techniques to the optical couplers, such techniques are typically not powerful enough to correct both the aberrations and the shift in focal plane between the visible and NIR images produced with such instruments. A novel optical coupler capable of correcting for the optical aberrations and for the difference in visible and NIR focal plane locations introduced when using conventional optical instruments is, consequently, highly desirable.

SUMMARY OF THE INVENTION

The invention described in this disclosure is directed to an optical coupler that corrects for both the optical aberrations and the shift in focal plane between the visible and NIR images that is introduced by conventional optical instruments and enables those instruments to be used with a VIS NIR imaging system of the type described in the Annex to this application.

Although well-corrected for visible light imaging and producing substantially coincident focal plane locations for images at wavelengths throughout the visible spectrum (400-700 nm), at NIR wavelengths (700-900 nm) conventional optical instruments will project poorly corrected images at focal plane locations substantially displaced from those for the visible spectrum images. This is particularly problematic for imaging systems using a single color image sensor onto which both visible light and NIR light images are projected. An exemplary single color image sensor is described in the Annex to this application. Conventional optical instruments are not compatible with such imaging systems without some correction to the NIR images that they project.

The disclosed system utilizes a combination of correction mechanisms in a novel optical coupler to address the multiple challenges in compensating for the NIR imaging properties of conventional optical instruments without degrading the performance in the visible spectrum. Specifically, this VIS NIR optical coupler splits the optical path into visible and NIR paths within the optical coupler and thereby enables distributed correction for path length differences between the visible and NIR spectrum. The separate visible and NIR optical paths are recombined after compensation for optical path length difference and are then projected by a lens assembly that corrects for aberrations in the NIR without compromising the performance in the visible spectrum.

BRIEF DESCRIPTION OF THE DRAWINGS

FIG. 6 shows ray tracing in an exemplary optical coupler capable of compensating for the difference in visible and NIR focal plane locations; and FIG. 7 shows characteristic design parameters for an exemplary system according to the invention.

DETAILED DESCRIPTION

Figure 1:
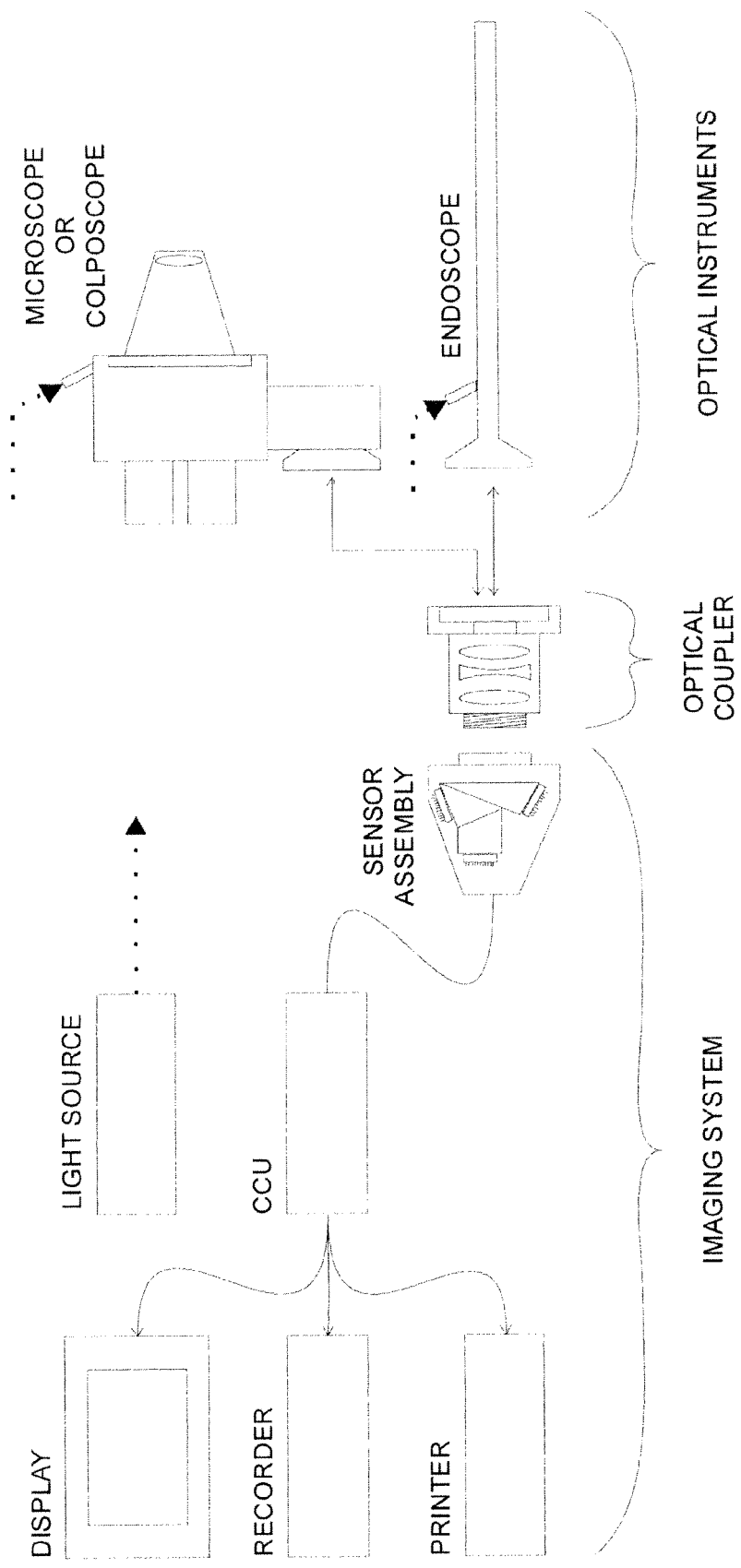
FIG. 1 shows an imaging system operatively connected to an endoscope using an optical coupler according to the invention.

FIG. 1 depicts a typical configuration of an optical instrument, optical coupler and imaging system. The components may include an optical instrument such as the endoscope shown or another optical image transmitting instrument such as a microscope, a colposcope, or the like. The optical instrument is connected to the imaging system by an optical coupler that projects an optical image from the optical instrument onto the imaging system's sensor assembly. The sensor assembly may be a single or multi-sensor (e.g. 3-chip) assembly composed of CCD or CMOS or other solid state image sensors. The sensor assembly converts the optical image into electrical signals which may subsequently be processed and outputted to a display, recording and/or printing device.

The conventional optical coupler used with visible light imaging systems typically consists of a multi-element lens assembly with either a fixed or adjustable focus. More sophisticated couplers may incorporate zoom lens designs. As with conventional optical instruments, optical couplers used with visible light imaging systems are also typically well-corrected throughout the visible spectrum and will faithfully project a well-corrected visible light image from an optical instrument onto the imaging system's sensor assembly. Given their relatively simple design, however, there are insufficient parameters by which the optical properties (i.e. the lens design) of conventional optical couplers can be adjusted to compensate for both the aberrations and the focal plane shifts incurred with NIR images produced by conventional optical instruments without negatively affecting the performance of the coupler in the visible spectrum.

Figure 2:
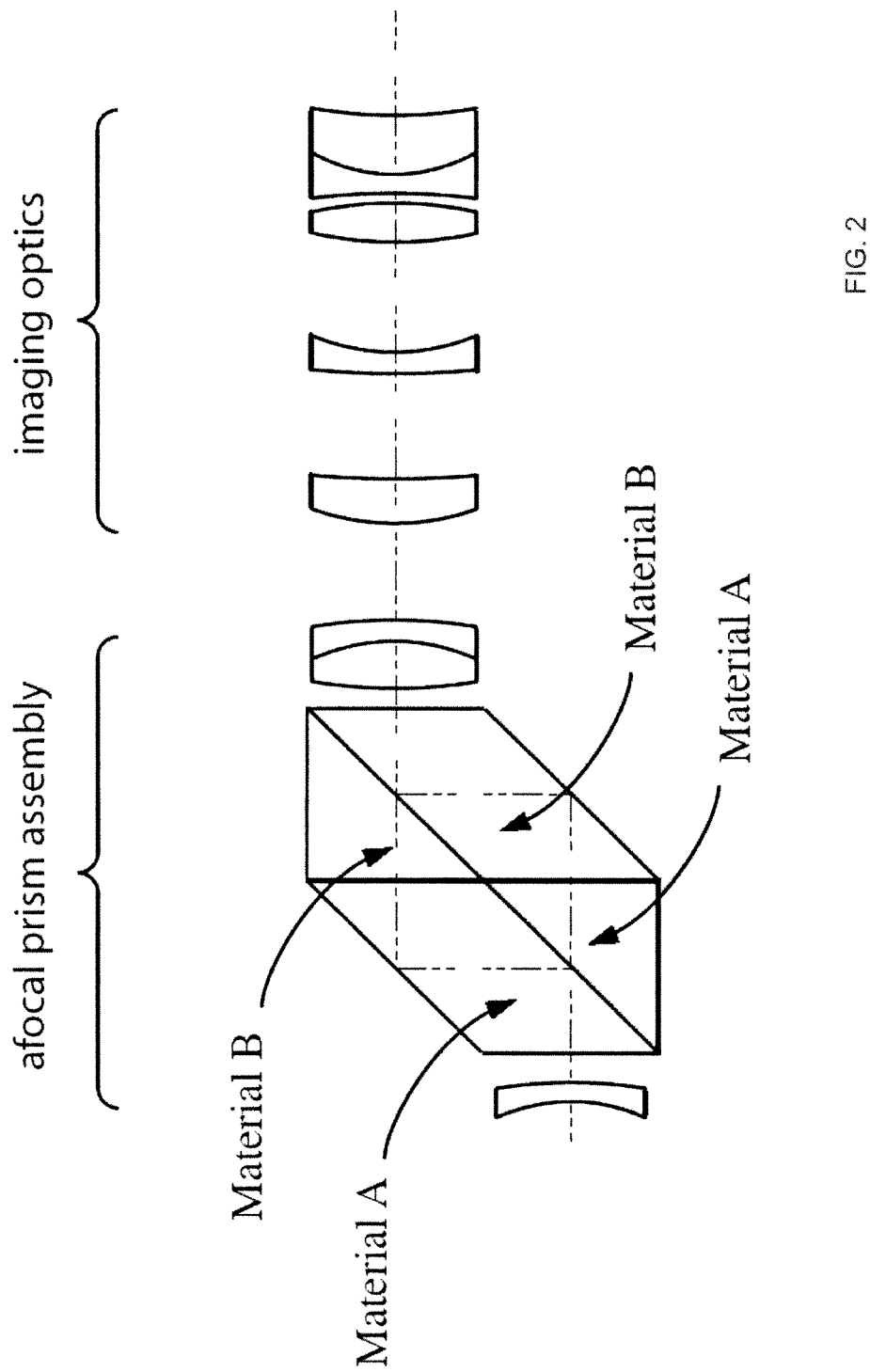
FIG. 2 shows an embodiment of a VIS NIR optical coupler with an afocal prism assembly.

FIG. 2 depicts an embodiment of a VIS NIR optical coupler comprising
- an afocal prism assembly that compensates for the optical path length differences between the VIS and NIR focal plane locations produced by the optical instrument, and
- imaging optics, that correct for the aberrations in the visible and NIR images produced by the optical instruments and project those corrected images onto the imaging system's sensor assembly.

Figure 3:
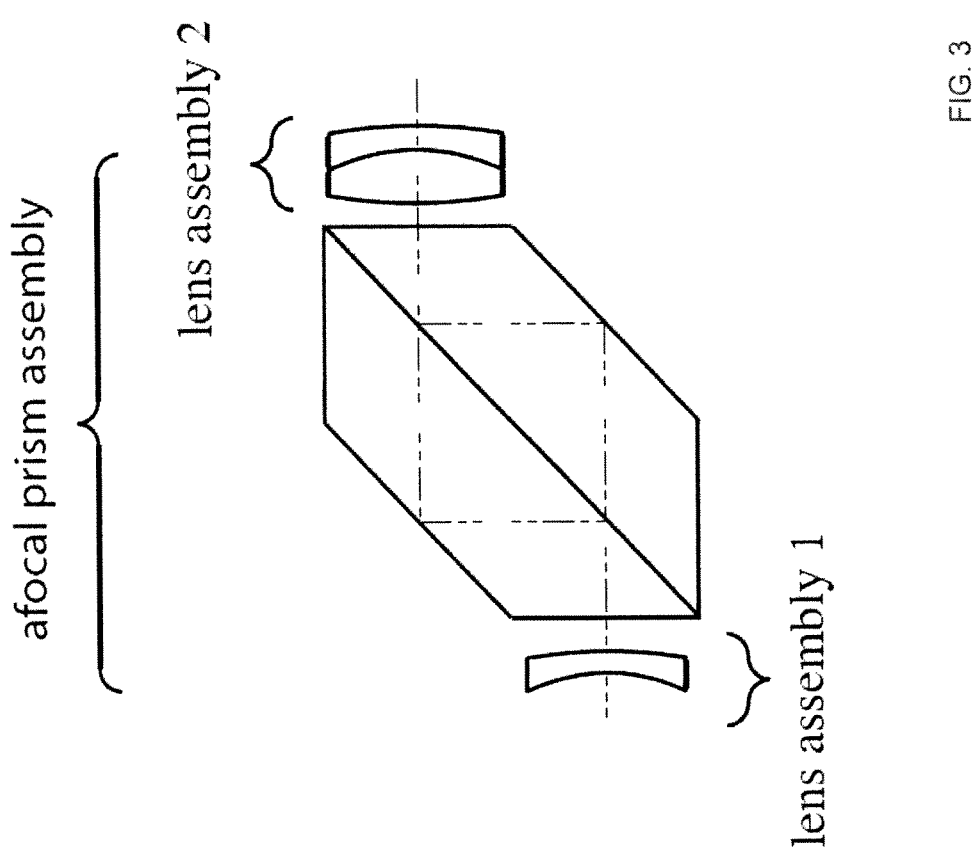
FIG. 3 shows the afocal prism assembly of FIG. 2 in more detail.

One embodiment of the afocal prism assembly is depicted in FIG. 3. This afocal assembly includes a first lens or lens assembly that imparts some increased optical power to the image forming rays emitted by the optical instrument, a path length compensating multi-element prism to compensate for the optical path length differences between the VIS and NIR focal plane locations produced by the optical instrument, and a lens or lens assembly of the opposite power following the multi-element prism. The multi-element prism is composed of sections of material having different indices of refraction, (Material A and Material B) and having dichroic coatings on the diagonal surface between sections such that one half of the diagonal surface is coated with a short pass coating transmitting visible light and reflecting NIR light and the other half is coated with a long pass coating transmitting NIR light and reflecting visible light. The relationship between the dichroic coatings and the indices of refraction for the prism materials are such that if the index of refraction for Material A is greater than for Material B, light from the optical instrument will encounter a long pass coating (i.e. passes NIR and reflects VIS) at the first dichroic diagonal surface in the multi-element prism and a short pass (i.e. passes VIS and reflects NIR) at the second dichroic diagonal surface. The location of the dichroics is reversed for the opposite relationship between the indices of refraction of Materials A and B.

Figure 4:
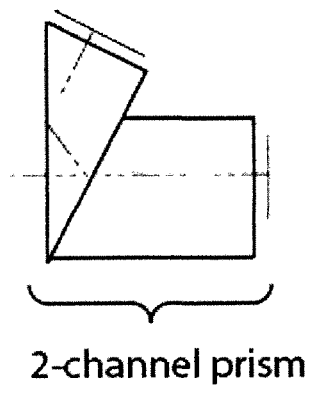
FIG. 4 shows exemplary embodiments of multi-element prisms for use with a sensor assembly incorporating multiple sensors.
Figure 4:
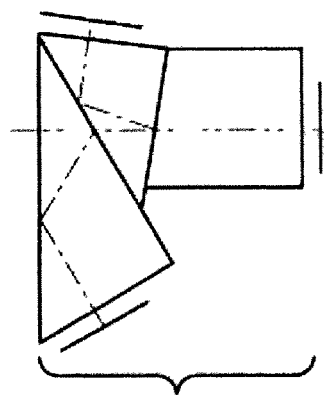
Figure 4:
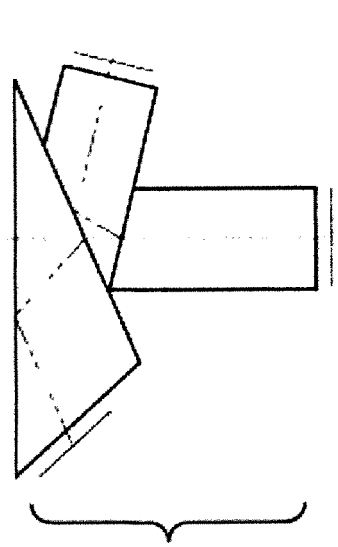
Figure 4:
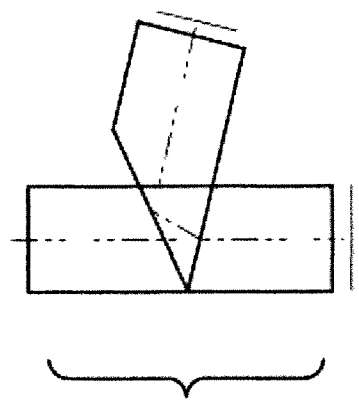

The imaging lens assembly (FIG. 2) accepts the image forming rays from the optical instrument projected through the prism assembly and focuses an optical image corrected for visible and NIR wavelengths onto the imaging system's sensor assembly. This assembly may be mounted in the optical coupler such that its position along the optical axis can be adjusted (i.e. the image can be focused onto the sensor assembly for a range of object distances). The imaging lens assembly may further be designed for use with a sensor assembly incorporating a multi-channel prism, a number of which are shown in FIG. 4. The imaging system disclosed in the Annex incorporates a sensor assembly with a 3 channel (RGB) prism, but this optical coupler may also be used with two or four or more channel sensor assembly.

The properties and operation of the afocal prism assembly can then be further described as follows:

The light output of optical instruments is typically collimated or nearly collimated and the first lens (or lens assembly) in the afocal prism assembly imparts a negative (or positive) optical power to the light emitted from the optical instrument. The diverging (or converging) light is subsequently transmitted through the path length compensating prism. As can be seen by the ray diagrams in FIG. 6, the afocal prism assembly corrects for the difference in the focal plane location of the NIR and visible light images projected by conventional optical instruments. Since the light entering the prism assembly is diverging (or converging), by causing the NIR and visible light to traverse separate optical paths through materials with different refractive indices, the difference in focal plane location can be compensated for before recombining the two optical paths. The second lens (or lens assembly) in the afocal prism assembly subsequently offsets the optical power induced by the first lens (or lens assembly) causing this assembly to be substantially afocal.

The properties of the multi-element prism are determined by such factors as the optical power of the light bundle emitted by the first lens assembly, the path length difference between the focal planes of the visible and NIR images projected by the optical instruments, the practical size constraints and ranges of refractive indices of glasses, and the desired effective focal length (or magnification) of the optical coupler. The materials of the imaging optics are consequently selected such that the entire optical system, including the optical instrument, is achromatic for the visible and NIR spectra of interest. Nevertheless, the VIS and NIR image focused onto the imaging system's sensor assembly will show a slight lateral displacement between the visible and NIR components as a consequence of traversing the multi-element prism. Additionally, there will also be residual magnification differences in the resulting images. Since the visible and NIR images are acquired independently in a VIS NIR imaging system, such as the one described in the Annex, it is possible to compensate for slight lateral displacements or residual magnification differences between the visible and NIR image components by means of image processing software. These means of registration correction and image scaling in software are commonly understood and practiced by those skilled in the art and require no further explanation here.

Figure 5A:
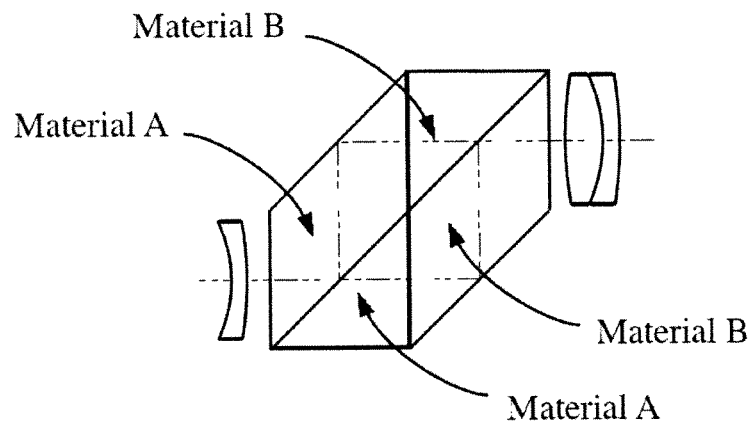
FIG. 5 shows alternative embodiments of the multi-element prism.
Figure 5B:
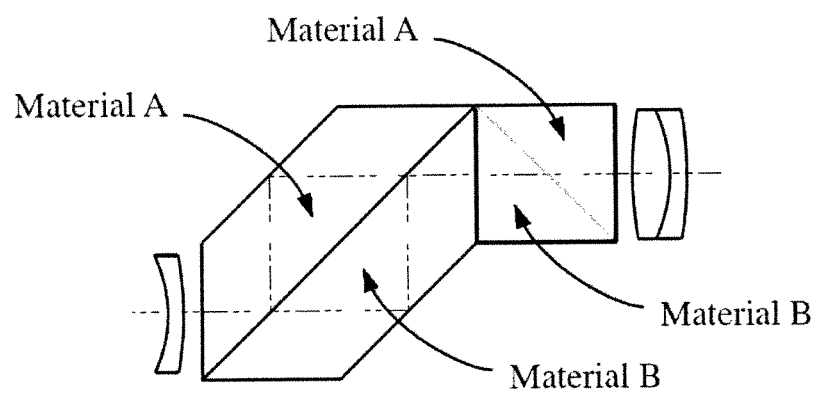

Alternative embodiments of the multi-element prism are shown in FIGS. 5a and 5b. In these embodiments, the lateral displacement introduced by the prism assembly in the first embodiment is better corrected by utilizing a more sophisticated design. The lateral displacement between the visible and NIR images is minimized by providing sections within (FIG. 5a), or in addition to the multi-element prism (FIG. 5b) that better compensate for any lateral shifts that are induced as the image rays traverse the prism assembly. Again, any residual lateral displacements or magnification differences between the visible and NIR image components may be further corrected by means of image processing software.

FIG. 6 provides a specific example of an optical coupler that can be used to compensate for the difference in visible (FIG. 6b) and NIR (FIG. 6c) focal plane locations introduced when using conventional optical instruments. The optical coupler has a total of 34 optical surfaces with characteristic physical properties (radius, thickness, material, diameter) listed in FIG. 7a for visible light and in FIG. 7b for NIR light. The optical surfaces are numbered from left to right in FIG. 7. The block on the right represents the multi-channel prism (see FIG. 4) to which the CCDs are attached. However, the reference numbers are omitted from FIG. 6 so as not to obscure the drawing. Performance metrics shown for this sample design are provided in FIGS. 6d-e.

Under certain circumstances there may be difference in magnification between the two VIS and NIR images formed on the detector. This difference in magnification could be addressed by processing the NIR signal separately and matching (e.g., electronically using known edge detection and resizing algorithms) the size of the NIR image to that of the VIS image.

Most remaining optical aberrations not related to the difference in magnification/focal point between the VIS and NIR images, commonly called Seidel aberrations, such as coma, astigmatism, spherical aberration, etc., can be reduced to an acceptable amount using the degrees of freedom in the lens assembly.

The Annex to this disclosure, which includes 9 sheets of drawings, forms an integral part of the disclosure, and its content is incorporated herein in its entirety as if set forth herein.

While the invention has been disclosed in connection with the preferred embodiments shown and described in detail, various modifications and improvements thereon will become readily apparent to those skilled in the art.

The invention claimed is:

1. An optical coupler comprising:
an afocal prism assembly configured to receive light from an optical instrument, the light from the optical instrument including visible light and near-infrared light having different optical path lengths to respective visible and near-infrared focal plane locations, the prism assembly being configured to cause the visible light and near-infrared light to traverse separate optical paths to correct for path length difference such that visible and near infrared images can be formed on substantially the same image plane.

2. The optical coupler of claim 1, wherein the prism assembly comprises adjoining prisms, with at least one of the adjoining prisms made of a different material having different indices of refraction than the other adjoining prisms.

3. The optical coupler of claim 2, wherein the adjoining prisms contact each other and wherein interfaces between the adjoining prisms have an optical coating constructed to reflect one of the visible light and the near-infrared light and to transmit the other of the visible light and the near-infrared light.

4. The optical coupler of claim 2, wherein the adjoining prisms comprise two dove prisms made of different materials, with the bases of the dove prisms contacting each other.

5. The optical coupler of claim 4, wherein each dove prism is composed of two prisms having different shapes and being made of different materials, with the first of the two prisms being a rectangular prism made of a first material and the second prism being a parallelepiped prism to form in combination the dove prism.

6. The optical coupler of claim 1, wherein the afocal prism assembly is configured to recombine the separated optical paths of the visible light and near-infrared light.

7. The optical coupler of claim 6, further comprising:
an imaging lens assembly configured to receive the corrected and recombined visible and near infrared light from the afocal prism assembly and to focus an optical image on a focal plane, the optical image including a visible light image and a near infrared image.

8. The optical coupler of claim 1, wherein the afocal prism assembly comprises:
a first lens assembly configured to impart increased power to the visible light and near-infrared light received from the optical instrument,
a multi-element prism configured to receive the visible light and the near-infrared light of increased power from the first lens assembly and cause the visible light and near-infrared light to traverse separate optical paths to correct for path length difference such that visible and near infrared images can be formed on substantially the same image plane, and
a second lens assembly configured to receive the corrected visible light and near-infrared light from the multi-element prism and to impart a power to the visible light and near-infrared light that is opposite to that of the first lens assembly.

9. An optical coupler comprising:
an afocal prism assembly configured to receive light from an optical instrument, the light from the optical instrument including visible light and near-infrared light having different optical path lengths to respective visible and near-infrared focal plane locations, the afocal prism assembly including
a first lens assembly configured to impart increased power to the visible light and near-infrared light received from the optical instrument,
a multi-element prism configured to receive the visible light and the near-infrared light of increased power from the first lens assembly and cause the visible light and near-infrared light to traverse separate optical paths to correct for path length difference such that visible and near infrared images can be formed on substantially the same image plane, and
a second lens assembly configured to receive the corrected visible light and near-infrared light from the multi-element prism and to impart a power to the visible light and near-infrared light that is opposite to that of the first lens assembly; and
an imaging lens assembly configured to receive the visible and the near infrared light from the second lens assembly and to focus an optical image on a focal plane, the optical image including a visible light image and a near infrared image.

10. The optical coupler of claim 9, wherein the afocal prism assembly is configured to recombine the separated optical paths of the visible light and near-infrared light.

11. The optical coupler of claim 9, wherein the imaging lens assembly is configured to correct for aberrations in the near-infrared image without compromising the visible image.

12. An optical imaging assembly comprising:
an endoscope configured to acquire visible light and near-infrared light from a target, the visible light and the near-infrared light having different optical path lengths to respective visible and near-infrared focal plane locations;
an afocal prism assembly configured to receive the visible light and the near-infrared light from the endoscope and to cause the visible light and near-infrared light to traverse separate optical paths to correct for path length difference such that visible and near infrared images can be formed on substantially the same image plane;
an imaging lens assembly configured to receive the visible and the near infrared light from the afocal prism assembly assembly and to focus an optical image on a focal plane, the optical image including a visible light image and a near infrared image.

13. The optical coupler of claim 12, wherein the image plane is an optical input surface of an image sensor sensitive in the visible and near-infrared spectral range.

14. The optical coupler of claim 12, wherein the image plane is formed by separate surfaces of a multi-channel prism, with the separate surfaces having image sensors which are sensitive to different wavelength bands in the visible and near-infrared spectral range.

15. The optical imaging system of claim 12, wherein the afocal prism assembly is configured to recombine the separated optical paths of the visible light and near-infrared light.

16. The optical imaging system of claim 12, wherein the imaging lens assembly is configured to correct for aberrations in the near-infrared image without compromising the visible image.

17. The optical imaging assembly of claim 12, wherein the afocal prism assembly comprises:
- a first lens assembly configured to impart increased power to the visible light and near-infrared light received from the optical instrument,
- a multi-element prism configured to receive the visible light and the near-infrared light of increased power from the first lens assembly and cause the visible light and near-infrared light to traverse separate optical paths to correct for path length difference such that visible and near infrared images can be formed on substantially the same image plane, and
- a second lens assembly configured to receive the corrected visible light and near-infrared light from the multi-element prism and to impart a power to the visible light and near-infrared light that is opposite to that of the first lens assembly.

18. The optical imaging assembly of claim 17, wherein the multi-element prism comprises:
- a first element made of a first material having a first index of refraction, the first element being arranged to receive light from the first lens assembly;
- a second element made of second material having a second index of refraction, the second index of refraction being different from the first index of refraction, the second element being arranged to receive light from the first element;
- a diagonal surface between the first element and the second element, a first portion of the diagonal surface having a first coating, and a second portion of the diagonal surface having a second coating,
- wherein when the first index of refraction is greater than the second index of refraction, the visible light and the near-infrared light will encounter a long pass coating at the first portion of the diagonal surface and a short pass coating at the second portion of the diagonal surface, and
- wherein when the second index of refraction is greater than the first index of refraction, the visible light and the near-infrared light will encounter a short pass coating at the first portion of the diagonal surface and a long pass coating at the second portion of the diagonal surface.

19. The optical imaging assembly of claim 12, further comprising an imaging processor configured to compensate for lateral differences or residual magnification differences between the visible light image and the near-infrared image.

* * * * *